United States Patent
Turowski-Wanke et al.

(10) Patent No.: US 6,291,422 B1
(45) Date of Patent: Sep. 18, 2001

(54) SURFACTANT-CONTAINING FORMULATIONS

(75) Inventors: Angelika Turowski-Wanke, Kelkheim; Matthias Löffler, Niedernhausen; Hans Jürgen Scholz, Alzenau; Werner Skrypzak, Hofheim/Lorsbach; Bernd Papenfuhs, Obertshausen, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/269,588

(22) PCT Filed: Sep. 24, 1997

(86) PCT No.: PCT/EP97/05227

§ 371 Date: May 17, 1999

§ 102(e) Date: May 17, 1999

(87) PCT Pub. No.: WO98/14542

PCT Pub. Date: Apr. 9, 1998

(30) Foreign Application Priority Data

Sep. 30, 1996 (DE) .............................................. 196 40 186

(51) Int. Cl.[7] ................................. C11D 1/10; C11D 1/52; C07C 233/00; B01F 17/28

(52) U.S. Cl. .......................... 510/535; 510/126; 510/220; 510/237; 510/276; 510/350; 510/353; 510/433; 510/521; 510/313; 510/499; 554/66

(58) Field of Search ................................... 510/126, 220, 510/237, 276, 350, 353, 433, 521, 535, 313, 499; 554/66

(56) References Cited

U.S. PATENT DOCUMENTS 4,021,539 * 5/1977 Moller et al. ........................... 424/73
5,744,644 * 4/1998 Papenfuhs ............................. 564/444
5,760,258 * 6/1998 Papenfuhs ............................... 554/66

FOREIGN PATENT DOCUMENTS

| 4238211 | 1/1994 | (DE) . |
| 19512299 | 10/1996 | (DE) . |
| 19519705 | 12/1996 | (DE) . |

OTHER PUBLICATIONS

International Search Report, for PCT/EP 97/05227 (equivalent to USSN 09/269,588, dated Feb. 25, 1998.

* cited by examiner

*Primary Examiner*—Yogendra Gupta
*Assistant Examiner*—Brian P. Mruk
(74) *Attorney, Agent, or Firm*—Hesna J. Pfeiffer; Scott E. Hanf

(57) ABSTRACT

The invention relates to surfactant-containing formulations which comprise, as surfactant, an N-(3-dialkylamino)propyl-N-polyhydroxyalkylcarboxamide of the formula

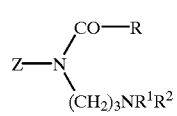

(1)

where R is an aliphatic radical having from 8 to 24 carbon atoms, $R^1$ and $R^2$, which are identical or different, are alkyl groups having from 1 to 4 carbon atoms or hydroxyalkyl groups having from 2 to 4 carbon atoms, and Z is a linear polyhydroxyhydrocarbon radical having at least 3 OH groups, which may also be alkoxylated, and also to their acid addition products. The surfactant-containing formulations are used in industrial and standard household surfactant compositions.

6 Claims, No Drawings

SURFACTANT-CONTAINING FORMULATIONS

BACKGROUND OF THE INVENTION

The use of fatty acid N-alkylpolyhydroxyalkylamides and, in particular, of fatty acid N-methylglucamide is already known from DE-A-4 430 085; DE-A-4 326 950; DE-A-4 432 366; DE-A-4 424 823; WO 92/6153; WO 92/6156; WO 92/6157; WO 92/6158; WO 92/6159 and WO 92/6160. As well as their high detergency, important advantages of the fatty acid N-methylglucamides are their good biodegradability and the fact that they can be prepared from renewable raw materials. The use of this group of substances as thickeners is also known (EP-A-285 768).

A disadvantage for the use and formulation is the limited solubility of these substances, particularly those having a chain length greater than C16. At relatively high concentrations in water they can only be handled with difficulty because of their high viscosity. Relatively high temperatures, which reduce the viscosity, however, lead to increased hydrolysis.

DE-A-4 238 207 and DE-A-4 238 211 disclose the use of fatty acid polyhydroxyalkylamides as surfactants, which differ from the previously mentioned fatty acid N-alkylpolyhydroxyalkylamides by virtue of the fact that the alkyl group is substituted by a dialkylamino group. Furthermore, these sugar surfactants are quaternized.

SUMMARY OF THE INVENTION

It has now been found that the sugar surfactants described in DE-A-4 238 207 and DE-A-4 238 211 are also excellent surfactants in their nonquaternized form. This finding is surprising since the cited prior art makes no mention of the use of the nonquaternized compounds of this type as surfactants.

The invention provides surfactant-containing formulations which comprise, as surfactant, an N-(3-dialkylamino) propyl-N-polyhydroxyalkylcarboxamide of the formula

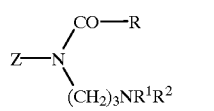

(1)

where R is an aliphatic radical having from 8 to 24 carbon atoms, $R^1$ and $R^2$, which are identical or different, are alkyl groups having from 1 to 4 carbon atoms or hydroxyalkyl groups having from 2 to 4 carbon atoms, and Z is a linear polyhydroxyhydrocarbon radical having at least 3 OH groups, which may also be alkoxylated, and also their acid addition products.

DESCRIPTION OF THE PREFERRED EMBODIMENTS

Preference is given to compounds of the formula 1 in which $R^1$ and $R^2$ are methyl, and Z is the residue of a sugar alcohol derived from a reducing mono- or disaccharide, in particular from glucose.

These compounds are prepared as stated in DE-A-19 51 2249 by acylating an amine of the formula (2)

(2)

with introduction of the radical R—CO, where R, $R^1$, $R^2$ and Z are as defined above.

The acid addition products are then obtained in an additional step by adding a suitable acid. Examples of such acids are mineral acids, such as hydrochloric acid, or organic acids, such as carboxylic acids (acetic acid), hydroxycarboxylic acids (lactic acid), branched, linear, saturated or unsaturated fatty acids, dicarboxylic acids (maleic acid, succinic acid, adipic acid), polycarboxylic acids (citric acid) or amino acids and derivatives thereof.

Compared with the non-basically substituted known compounds, these compounds have the added advantage that, for matching the hydrophilic properties, not only is the radical Z available, but also the basically substituted alkylene radical, and so the hydrophilic properties can be better tailored than the hydrophobic properties—effected by means of the radical R. The compounds of the formula 1 and their acid addition products are generally suitable as surfactants since they have excellent surfactant properties, such as very good foaming ability, good fat dispersibility (soil titration) and good detergency, coupled with high stability to water hardness and good skin compatibility.

They are suitable for all types of surfactant-containing formulations, in particular for cosmetic cleansing formulations and household cleaners. The formulations according to the invention preferably comprise the compounds of the formula 1 in an amount of from 0.1 to 99% by weight, in particular from 1 to 50% by weight.

Preferred formulations according to the invention are pulverulent universal detergents (from 1 to 30% by weight), liquid universal detergents (from 1 to 70% by weight), liquid light-duty detergents (from 1 to 50% by weight), hand modifiers (from 1 to 50% by weight), manual dishwashing compositions (from 1 to 50% by weight), toilet cleaners (from 1 to 50% by weight), liquid cleaners and disinfectants (from 1 to 30% by weight), bar soaps of the combination bar type (from 1 to 2% by weight), syndet soaps (from 1 to 2% by weight), hair shampoos (from 1 to 30% by weight), hair rinses (from 1 to 30% by weight), hair dyes (from 1 to 30% by weight), hair-waving compositions (from 1 to 30% by weight), foam baths (from 1 to 30% by weight), face cleansers (from 1 to 30% by weight), textile and fiber auxiliaries (from 1 to 30% by weight), leather greasing agents (from 1 to 30% by weight), flotation auxiliaries (from 1 to 30% by weight) and auxiliaries for dewatering sludges. The percentages in brackets indicate the preferred content of surfactant of the formula 1 in these formulations.

The formulations according to the invention may comprise a compound of the formula 1 or their acid addition products as the sole surfactant, but these surfactants are preferably combined with other customary anionic, nonionic, cationic and/or amphoteric surfactants. The mixing ratio between the surfactants of the formula 1 or their acid addition products and the other surfactants can fluctuate within wide limits, for example in the weight ratio from 1 to 99 to 99 to 1, preferably from 80 to 20 to 20 to 80. The total concentration of surfactants in the formulations according to the invention can be from 1 to 99% by weight, preferably from 5 to 50% by weight.

Suitable anionic surfactants include sulfonates, sulfates, carboxylates, phosphates and mixtures of the above compounds. Suitable cations in this case are alkali metals such as, for example, sodium or potassium, or alkaline earth metals such as, for example, calcium or magnesium, and ammonium, substituted ammonium compounds, including mono-, di- or triethanolammonium cations and mixtures of the cations. The following types of anionic surfactants are of particular interest: alkyl ester sulfonates, alkylsulfates, alkyl ether sulfates, alkylbenzenesulfonates, secondary alkanesulfonates and soaps as described below.

Alkyl ester sulfonates include linear esters of $C_8$–$C_{20}$-carboxylic acids (i.e. fatty acids) which are sulfonated using gaseous $SO_3$, as described in The Journal of the American Oil Chemists' Society 52 (1975), pp. 323–329. Suitable starting materials are natural fats such as, for example, tallow, palm oil or coconut oil, but they can also be synthetic. Preferred alkyl ester sulfonates, particularly for detergent applications, are compounds of the formula

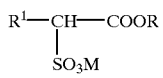

where $R^1$ is a $C_8$–$C_{20}$-hydrocarbon radical, preferably alkyl, and R is a $C_1$–$C_6$-hydrocarbon radical, preferably alkyl. M is a cation which forms a water-soluble salt with the alkyl ester sulfonate. Suitable cations are sodium, potassium, lithium or ammonium cations, such as monoethanolamine, diethanolamine and triethanolamine. $R^1$ is preferably $C_{10}$–$C_{16}$-alkyl and R is preferably methyl, ethyl or isopropyl. Particular preference is given to methyl ester sulfonates where $R^1$ is $C_{10}$–$C_{16}$-alkyl.

Alkylsulfates are in this case water-soluble salts or acids of the formula $ROSO_3M$, where R is preferably a $C_{10}$–$C_{24}$-hydrocarbon radical, preferably $C_{10}$–$C_{20}$-alkyl or hydroxyalkyl, particularly preferably $C_{12}$–$C_{18}$-alkyl or -hydroxyalkyl. M is hydrogen or a cation, e.g. an alkali metal cation (e.g. sodium, potassium, lithium), ammonium or substituted ammonium, e.g. methyl-, dimethyl- and trimethylammonium cations and quaternary ammonium cations, such as tetramethylammonium and dimethylpiperidinium cations and quaternary ammonium cations, derived from alkylamines such as ethylamine, diethylamine, triethylamine and mixtures thereof. Alkyl chains with $C_{12}$–$C_{16}$ are preferred for low wash temperatures (e.g. below about 50° C.) and alkyl chains with $C_{16}$–$C_{18}$ are preferred for higher wash temperatures (e.g. above about 50° C.).

Alkyl ether sulfates are water-soluble salts or acids of the formula $RO(A)_mSO_3M$, where R is an unsubstituted $C_{10}$–$C_{24}$-alkyl or hydroxyalkyl radical, preferably a $C_{12}$–$C_{20}$-alkyl or hydroxyalkyl radical, particularly preferably $C_{12}$–$C_{18}$-alkyl or -hydroxyalkyl radical. A is an ethoxy or propoxy unit, m is a number greater than 0, preferably between about 0.5 and about 6, particularly preferably between about 0.5 and about 3, and M is a hydrogen atom or a cation such as, for example, sodium, potassium, lithium, calcium, magnesium, ammonium or a substituted ammonium cation. Specific examples of substituted ammonium cations are methyl-, dimethyl-, trimethylammonium and quaternary ammonium cations such as tetramethylammonium and dimethylpiperidinium cations, and those which are derived from alkylamines, such as ethylamine, diethylamine, triethylamine and mixtures thereof. Examples which may be given are $C_{12}$–$C_{18}$ fatty alcohol ether sulfates where the content of ethylene oxide is 1, 2, 2.5, 3 or 4 mol per mole of fatty alcohol ether sulfate, and where M is sodium or potassium.

In secondary alkanesulfonates, the alkyl group can either be saturated or unsaturated, branched or linear and may be substituted by a hydroxyl group. The sulfo group can occupy any position over the whole carbon chain, except that the primary methyl groups at the start and end of the chain have no sulfo groups. The preferred secondary alkanesulfonates contain linear alkyl chains having from about 9 to 25 carbon atoms, preferably from about 10 to about 20 carbon atoms and particularly preferably from about 13 to 17 carbon atoms. Examples of the preferred cation are sodium, potassium, ammonium, mono-, di- or triethanolammonium, calcium or magnesium.

Other suitable anionic surfactants are alkenyl- or alkylbenzenesulfonates. The alkenyl or alkyl group can be branched or linear and may be substituted by a hydroxyl group. The preferred alkylbenzenesulfonates contain linear alkyl chains having from about 9 to 25 carbon atoms, preferably from about 10 to about 13 carbon atoms, and the cation is sodium, potassium, ammonium, mono-, di- or triethanolammonium, calcium or magnesium and mixtures thereof. For mild surfactant systems, magnesium is the preferred cation while sodium is preferred for standard washing applications. The same applies to alkenylbenzenesulfonates.

The term anionic surfactants also includes olefinsulfonates, which are obtained by sulfonation of $C_{12}$–$C_{24}$-, preferably $C_{14}$–$C_{16}$-α-olefins with sulfur trioxide and subsequent neutralization. Owing to the preparation process, these olefinsulfonates may contain relatively small amounts of hydroxyalkanesulfonates and alkanedisulfonates. Specific mixtures of α-olefin sulfonates are described in U.S. Pat. No. 3,332,880.

Further preferred anionic surfactants are carboxylates, for example fatty acid soaps and comparable surfactants. The soaps can be saturated or unsaturated and can contain various substituents, such as hydroxyl groups or α-sulfonate groups. Preference is given to linear saturated or unsaturated hydrocarbon radicals having from about 6 to about 30 carbon atoms, preferably from about 10 to about 18 carbon atoms.

Other suitable anionic surfactants are salts of acylaminocarboxylic acids, the acyl sarcosinates obtained by reacting fatty acid chlorides with sodium sarcosinate in an alkaline medium; fatty acid-protein condensation products obtained by reacting fatty acid chlorides with oligopeptides; salts of alkylsulfamidocarboxylic acids, salts of alkyl and alkylaryl ether carboxylic acids, $C_8$–$C_{24}$-olefinsulfonates, sulfonated polycarboxylic acids prepared by sulfonation of the pyrolysis products of alkaline earth metal citrates, as described for example in GB-1,082,179; alkyl glycerol sulfates, fatty acyl glycerol sulfates, alkylphenol ether sulfates, primary paraffinsulfonates, alkylphosphates, alkyl ether phosphates, isethionates, such as acylisethionates, N-acyltaurides, alkylsuccinates, sulfosuccinates, monoesters of sulfosuccinates (particularly saturated and unsaturated $C_{12}$–$C_{18}$-monoesters) and diesters of sulfosuccinates (particularly saturated and unsaturated $C_{12}$–$C_{18}$-diesters), acylsarcosinates, sulfates of alkylpolysaccharides such as sulfates of alkylpolyglycosides, branched primary alkylsulfates and alkylpolyethoxycarboxylates such as those of the formula $RO(CH_2CH_2)_kCH_2COO^-M^+$, where R is $C_8$–$C_{22}$-alkyl, k is a number from 0 to 10 and M is a cation, resin acids or hydrogenated resin acids, such as rosin or hydrogenated rosin or tall oil resins and tall oil resin acids.

Further examples are described in Surface Active Agents and Detergents (Vol. I and II, Schwartz, Perry and Berch).

Examples of suitable nonionic surfactants are the following:

Polyethylene, polypropylene and polybutylene oxide condensates of alkylphenols.

These compounds comprise the condensation products of alkylphenols having a $C_6$–$C_{20}$-alkyl group, which can be either linear or branched, with alkene oxides. Preference is given to compounds containing about 5 to 25 mol of ethylene oxide per mole of alkylphenol. Commercially available surfactants of this type are, for example, Igepal® CO-630, Triton® X-45, X-114, X-100 and X102, and the ®Arkopal-N products from Hoechst AG.

Condensation products of aliphatic alcohols with from about 1 to about 25 mol of ethylene oxide.

The alkyl chain of the aliphatic alcohols can be linear or branched, primary or secondary, and generally contains from about 8 to about 22 carbon atoms. Particular preference is given to the condensation products of $C_{10}$–$C_{20}$-alcohols with from about 2 to about 18 mol of ethylene oxide per mole of alcohol. The alkyl chain can be saturated or unsaturated. The alcohol ethoxylates can have a narrow ("narrow range ethoxylates") or a broad ("broad range ethoxylates") homolog distribution of the ethylene oxide. Examples of commercially available nonionic surfactants of this type are Teritol® 15-S-9 (condensation product of a $C_{11}$–$C_{15}$ linear secondary alcohol with 9 mol of ethylene oxide), Tergitol® 24-L-NMW (condensation product of a $C_{12}$–$C_{14}$ linear primary alcohol containing 6 mol of ethylene oxide, having a narrow molecular weight distribution). This product class also includes the Genapol® products from Hoechst AG.

Condensation products of ethylene oxide with a hydrophobic base, formed by condensation of propylene oxide with propylene glycol.

The hydrophobic part of these compounds preferably has a molecular weight of between about 1500 and about 1800. The addition of ethylene oxide to this hydrophobic part leads to an improvement in the solubility in water. The product is liquid up to a polyoxyethylene content of about 50% of the total weight of the condensation product, which corresponds to a condensation with up to about 40 mol of ethylene oxide. Commercially available examples of this product class are the Pluronic® products from BASF and the ®Genapol PF products from Hoechst AG.

Condensation product of ethylene oxide with a reaction product of propylene oxide and ethylenediamine.

The hydrophobic unit of these compounds consists of the reaction product of ethylenediamine with excess propylene oxide and generally has a molecular weight of from about 2500 to about 3000. Ethylene oxide is added onto this hydrophobic unit until the product has a content of from about 40 to about 80% by weight of polyoxyethylene and a molecular weight of from about 5000 to about 11000. Commercially available examples of this compound class are the ®Tetronic products from BASF and the ®Genapol PN products from Hoechst AG.

Semipolar Nonionic Surfactants

This special category of nonionic compounds includes water-soluble amine oxides, water-soluble phosphine oxides and water-soluble sulfoxides, each having an alkyl radical of from about 10 to about 18 carbon atoms. Semipolar nonionic surfactants are also amine oxides of the formula

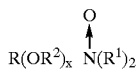

where R is an alkyl, hydroxyalkyl or alkylphenol group each having from about 8 to about 22 carbon atoms, $R^2$ is an alkylene or hydroxyalkylene group having from about 2 to 3 carbon atoms or mixtures thereof, each radical $R^1$ is an alkyl or hydroxyalkyl group having from about 1 to about 3 carbon atoms or a polyethylene oxide group having from about 1 to about 3 ethylene oxide units. The $R^1$ groups can be linked to one another via an oxygen or nitrogen atom and can therefore form a ring. Amine oxides of this type are, in particular, $C_{10}$–$C_{18}$-alkyldimethylamine oxides and $C_8$–$C_{12}$-alkoxyethyldihydroxyethylamine oxides.

Fatty Acid Amides

Fatty acid amides have the formula

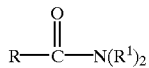

where R is an alkyl group having from about 7 to about 21, preferably from about 9 to about 17, carbon atoms, and each $R^1$ radical is hydrogen, $C_1$–$C_4$-alkyl, $C_1$–$C_4$-hydroxyalkyl or $(C_2H_4O)_xH$, where x varies from about 1 to about 3. Preference is given to $C_8$–$C_{20}$-amides, -monoethanolamides, -diethanolamides and -isopropanolamides.

Further suitable nonionic surfactants are, in particular, alkyl and alkenyl oligoglycosides and also fatty acid polyglycol esters or fatty amine polyglycol esters having in each case from 8 to 20, preferably from 12 to 18, carbon atoms in the fatty alkyl radical, alkoxylated triglycamides, mixed ethers or mixed formals, fatty acid N-alkylglucamides, protein hydrolyzates, phosphine oxides or dialkyl sulfoxides.

Typical examples of amphoteric and zwitterionic surfactants are alkyl betaines, alkylamido betaines, aminopropionates, aminoglycinates, or amphoteric imidazolinium compounds of the formula

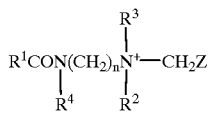

where $R^1$ is $C_8$–$C_{22}$-alkyl or -alkenyl, $R^2$ is hydrogen or $CH_2CO_2M$, $R^3$ is $CH_2CH_2OH$ or $CH_2CH_2OCH_2CH_2COOM$, $R^4$ is hydrogen, $CH_2CH_2OH$ or $CH_2CH_2COOM$, Z is $CO_2M$ or $CH_2CO_2M$, n is 2 or 3, preferably 2, M is hydrogen or a cation such as alkali metal, alkaline earth metal, ammonia or alkanolammonium.

Preferred amphoteric surfactants of this formula are monocarboxylates and dicarboxylates. Examples thereof are cocoamphocarboxypropionate, cocoamidocarboxypropionic acid, cocoamphocarboxyglycinate (also called cocoamphodiacetate) and cocoamphoacetate.

Other preferred amphoteric surfactants are alkyldimethylbetaines and alkyldipolyethoxybetaines containing an alkyl radical, which can be linear or branched, having from about 8 to about 22 carbon atoms, preferably having from 8 to 18 carbon atoms and particularly preferably having from about 12 to about 18 carbon atoms. These compounds are marketed, for example, by Hoechst AG under the trade name ®Genagen LAB.

Suitable cationic surfactants are substituted or unsubstituted straight-chain or branched quaternary ammonium salts of the type $R^1N(CH_3)_3^\oplus X^\ominus$, $R^1R^2N(CH_3)_2^\oplus X^\ominus$, $R^1R^2R^3N(CH_3)^\oplus X^\ominus$ or $R^1R^2R^3R^4N^\oplus X^\ominus$. The radicals $R^1$, $R^2$, $R^3$ and $R^4$ may, preferably independently of one another, be an unsubstituted alkyl having a chain length of between 8 and 24 carbon atoms, in particular between 10 and 18 carbon atoms, hydroxyalkyl having from about 1 to about 4 carbon atoms, phenyl, $C_2$- to $C_{18}$-alkenyl, $C_7$- to $C_{24}$-aralkyl, $(C_2H_4O)_xH$, where x is from about 1 to about 3, alkyl radicals comprising one or more ester groups, or cyclic quaternary ammonium salts. X is a suitable anion.

The formulations according to the invention comprise, depending on the intended use, as well as said surfactants, also the specific auxiliaries and additives in each case. Thus, for example, detergents and cleaner formulations comprise builders, salts, bleaches, bleach activators, optical brighteners, antiredeposition agents, solubilizers and enzymes.

Customary builders are sodium aluminum silicates (zeolites), phyllosilicates, phosphates, phosphonates, ethylenediaminetetraacetic acid, nitrilotriacetate, citric acid and/or polycarboxylate.

Suitable salts or extenders are, for example, sodium sulfate, sodium carbonate or sodium silicate (water glass). Typical individual examples of other additives which may be mentioned are sodium borate, starch, sucrose, polydextrose, TAED, stilbene compounds, methylcellulose, toluenesulfonate, cumenesulfonate, long-chain soaps, silicones, mixed ethers, lipases and proteases.

As well as said surfactants, the cosmetic or pharmaceutical formulations may comprise inter alia thickeners, moisturizers, biogenic active ingredients, film formers, conditioners, pearlizing agents, preservatives, perfume or dyes.

Hair shampoos, hair lotions or shower preparations and bath foams may comprise, as further auxiliaries and additives, emulsifiers such as, for example, alkoxylated fatty alcohols or sorbitan esters.

The superfatting agents may be substances such as, for example, polyoxyethylated lanolin derivatives, lecithin derivatives and fatty acid alkanolamides, the latter at the same time serving as foam stabilizers.

Examples of suitable thickeners are polysaccharides, in particular xanthan gum, guar, agar agar, alginates and Tyloses, carboxymethylcellulose and hydroxyethylcellulose, also high molecular weight polyethylene glycol mono- and diesters of fatty acids, polyacrylates, polyvinyl alcohol and polyvinylpyrrolidone and also electrolytes such as common salt and ammonium chloride.

Biogenic active substances are taken to mean, for example, plant extracts and vitamin complexes.

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives and similar compounds.

Another component which may be present in the formulation is a nonvolatile, liquid silicone. This can either be a polyalkylsiloxane, a polyarylsiloxane, a polyalkylarylsiloxane or a polyethersiloxane copolymer and is used in an amount of from about 0.1% to about 10.0%, preferably in an amount of from about 0.5% to about 5.0%. Mixtures of these liquids can also be used and are also advantageous for certain applications. The dispersed silicone particles should be insoluble in the shampoo matrix. The most important nonvolatile polyalkylsiloxanes which may be used are, for example, polydimethylsiloxanes having viscosities of from about 5 to about 600000 centistokes, preferably from 350 to about 100000 centistokes, at 25° C. A suitable essentially nonvolatile polyethersiloxane is, for example, a dimethylpolysiloxane modified using polypropylene oxide. It is also possible to use starting materials containing ethylene oxide and/or propylene oxide.

Suitable silicones are described, for example, in U.S. Pat. No. -2,826,551, U.S. Pat. No. 3,946,500, U.S. Pat. No. 4,364,837 and in GB-849,433.

According to the invention, it is also possible to use silicone gum. Silicone gums are described in U.S. Pat. No. 4,152,416 and in product data sheets SE 30, SE 33, SE 54 and SE 76 from General Electric. "Silicone gum" is a high molecular weight polydiorganosiloxane having a molar mass of from about 200000 to 1000000. Specific examples are polydimethylsiloxane, polydimethylsiloxane-methylvinylsiloxane copolymer, poly(dimethyl-siloxane)-(diphenyl)(methylvinylsiloxane) copolymer and mixtures thereof; mixtures of silicone liquids and silicone gums are also suitable.

Suitable preservatives are, for example, phenoxyethanol, formaldehyde solution, parabens, pentadiol or sorbic acid.

Suitable pearlizing agents are, for example, glycol distearic acid esters, such as ethylene glycol distearate, but also fatty acid monoglycol esters.

The dyes which may be used are those substances suitable and approved for cosmetic purposes, such as, for example, those listed in the publication "Kosmetische Färbemittel" [Cosmetic Colorants] from the Farbstoffkommission der Deutschen Forschungsgemeinschaft [Dyes Commission of the German Research Society], published by Verlag Chemie, Weinheim, 1984, pp. 81 to 106. These dyes are normally used in concentrations of from 0.001 to 0.1 % by weight, based on the total mixture.

The total amount of auxiliaries and additives can be from 1 to 50% by weight, preferably from 5 to 40% by weight, based on the surfactant-containing formulation.

EXAMPLES

The text below firstly gives a number of guide formulations for a series of specific formulations according to the invention. There then follows a number of defined formulations. In all of the examples, DMAP-GA is a sugar surfactant of the formula 1 as given above in which Z is a glucose residue, R is a $C_{12}/C_{14}$-fatty acid alkyl radical, unless stated otherwise, and $R^1$ and $R^2$ are in each case methyl. All percentages are percentages by weight.

| Composition | | |
|---|---|---|
| Shaving cream 1: | | |
| | Stearic acid | 20 to 40% |
| | Coconut fatty acid | 6 to 10% |
| | DMAP-GA | 1 to 45% |
| | Glycerol | 5 to 15% |
| | Potassium hydroxide | 2 to 6% |
| | Sodium hydroxide | 1 to 3% |
| | Plant or mineral oil | 1 to 5% |
| | Water | ad 100% |
| Shaving cream 2: | | |
| | Glycerol monostearate | 10 to 35% |
| | DMAP-GA | 1 to 45% |
| | Mineral oil | 5 to 15% |
| | Glycerol | 1 to 10% |
| | Water | ad 100% |
| Shaving lotion: | | |
| | Cellulose alkyl ether | 70 to 75% |
| | DMAP-GA | 1 to 5% |
| | Mineral oil | 10 to 20% |
| | Glycerol | 3 to 10% |
| | Water | ad 100% |
| Shower gel: | | |
| | Cellulose alkyl ether | 5 to 10% |
| | Na lauryl ether sulfate | 2 to 5% |
| | DMAP-GA | 1 to 45% |
| | Cocoylamidopropylbetaine | 8 to 15% |
| | Ethylene glycol distearate | 4 to 10% |
| | Isopropyl palmitate | 0.5 to 1% |
| | Moisturizer | 0.25 to 0.5% |
| | Preservative | 0.05 to 0.1% |
| | Sodium chloride | 3 to 5% |
| | Water | ad 100% |
| Clear all-purpose cleaner: | | |
| | DMAP-GA | 0.1 to 15% |
| | Anionic surfactants | 0 to 25% |
| | Amphoteric surfactants | 0 to 5% |
| | Nonionic surfactants | 0.5 to 15% |

-continued

| Composition | | |
|---|---|---|
| | Perfume oil | 0 to 1% |
| | Preservative | 0 to 1% |
| | Water | ad 100% |
| Manual dishwashing detergent: | | |
| | DMAP-GA | 0.1 to 15% |
| | Anionic surfactants | 0 to 40% |
| | Amphoteric surfactants | 0 to 15% |
| | Nonionic surfactants | 0 to 15% |
| | Amine oxides | 0 to 15% |
| | Perfume oil | 0 to 1% |
| | Preservative | 0 to 1% |
| | Sodium chloride | 0 to 5% |
| | Water | ad 100% |
| Liquid detergent: | | |
| | DMAP-GA | 0.1 to 15% |
| | Anionic surfactants | 0 to 40% |
| | Nonionic surfactants | 0 to 40% |
| | Extenders | 0 to 15% |
| | Enzymes | 0 to 15% |
| | Perfume oil | 0 to 1% |
| | Preservative | 0 to 1% |
| | Dye | 0 to 1% |
| | Water | ad 100% |

Example 1

Clear shower gel containing 15% active ingredient (detersive substance=DS):
Composition:

| A | DMAP-GA | 4.00% |
|---|---|---|
| B | Water | 48.85% |
| C | ® Genapol LRO liquid | 40.35% |
| | PEG 400 | 5.00% |
| | Perfume oil | 0.30% |
| | Preservative | q.s. |
| | Dye solution | q.s. |
| D | Citric acid | q.s. |
| E | Sodium chloride | 1.50% |

Preparation:

| I | Dissolve A in B with warming |
|---|---|
| II | Stir into I the components C one after the other |
| III | Regulate the pH using D, then adjust the viscosity using E |

Example 2

Clear shower gel containing 16% active ingredient (DS) without addition of sodium chloride
Composition:

| A | DMAP-GA | 6.00% |
|---|---|---|
| B | Water | 54.50% |
| C | ® Genapol LRO liquid | 30.00% |
| | ® Genagen CAB 818 | 5.00% |
| | ® Hostapon KCG | 4.00% |
| | Perfume oil | 0.50% |
| | Preservative | q.s. |
| | Dye solution | q.s |
| D | Citric acid | q.s. |

Preparation: As in Example 1

Example 3

Pearlescent shower preparation containing 16% active ingredient (DS) without addition of sodium chloride
Composition:

| A | DMAP-GA | 6.00% |
|---|---|---|
| B | Water | 54.70% |
| C | ® Genapol LRO liquid | 35.00% |
| | ® Genapol TSM | 4.00% |
| | Perfume oil | 0.30% |
| | Preservative | q.s. |
| | Dye solution | q.s. |
| D | Citric acid | q.s. |

Preparation as in Example 1

Example 4

Clear antidandruff shampoo containing 12.5% active ingredient (DS) without sodium chloride
Composition:

| A | DMAP-GA | 5.00% |
|---|---|---|
| | ® Octopirox | 0.50% |
| B | Water | 64.20% |
| C | ® Genapol LRO liquid | 30.00% |
| | Perfume oil | 0.30% |
| | Preservative | q.s. |
| | Dye solution | q.s. |
| D | Citric acid | |

Preparation as in Example 1

Example 5

Clear antidandruff shampoo containing 12.5% active ingredient (DS):
Composition:

| A | DMAP-GA | 2.50% |
|---|---|---|
| | ® Octopirox | 0.50% |
| B | Water | 57.10% |
| C | ® Genapol LRO liquid | 30.00% |
| | ® Medialan LD | 6.60% |
| | Perfume oil | 0.30% |
| | Preservative | q.s. |
| | Dye solution | q.s. |
| D | Citric acid | q.s. |
| E | Sodium chloride | 3.00% |

Preparation as in Example 1

Example 6

Clear antidandruff shampoo containing 12.5% active ingredient (DS):
Composition:

| A | DMAP-GA | 2.50% |
|---|---|---|
| | ® Octopirox | 0.50% |
| B | Water | 61.35% |
| C | ® Genapol LRO liquid | 30.00% |
| | ® Genapol SBE | 3.35% |
| | Perfume oil | 0.30% |
| | Preservative | q.s. |
| | Dye solution | q.s. |

-continued

| | | |
|---|---|---|
| D | Citric acid | q.s. |
| E | Sodium chloride | 2.00% |

Preparation as in Example 1

Example 7

Clear hair shampoo containing 15% active ingredient (DS):
Composition:

| | | |
|---|---|---|
| A | DMAP-GA | 5.00% |
| B | Water | 53.70% |
| C | ® Genapol LRO liquid | 35.00% |
| | ® Genapol SBE | 5.00% |
| | Perfume oil | 0.30% |
| | Preservative | q.s. |
| | Dye solution | q.s. |
| D | Citric acid | q.s. |
| E | Sodium chloride | 1.00% |

Preparation as in Example 1

Example 8

Clear all-purpose cleaner containing 10% active ingredient (DS)
Composition:

| | | |
|---|---|---|
| A | DMAP-GA | 1.50% |
| B | Water | 90.70% |
| C | ® LRO liquid | 1.50% |
| | ® Hostapur SAS 60 | 6.00% |
| | Perfume oil | 0.30% |
| | Preservative | q.s. |
| | Dye solution | q.s. |
| D | Citric acid | q.s. |

Preparation as in Example 1

Example 9

Clear dishwashing detergent containing 20% active ingredient (DS)
Composition:

| | | |
|---|---|---|
| A | DMAP-GA | 2.00% |
| B | Water | 62.70% |
| C | ® Genapol LRO liquid | 8.00% |
| | ® Hostapur SAS 60 | 25.00% |
| | Perfume oil | 0.30% |
| | Preservative | q.s. |
| | Dye solution | q.s. |
| D | Citric acid | q.s. |
| E | Sodium chloride | 2.00% |

Preparation as in Example 1

Example 10

Clear dishwashing detergent containing 32.5% active ingredient (DS) without addition of chloride
Composition:

| | | |
|---|---|---|
| A | DMAP-GA | 5.00% |
| B | Water | 53.70% |
| C | ® Genapol LRO liquid | 6.00% |
| | ® Hostapur SAS 60 | 35.00% |
| | Perfume oil | 0.30% |
| | Preservative | q.s. |
| | Dye solution | q.s. |
| D | Citric acid | q.s. |

Preparation as in Example 1

Example 11

Pearlescent shower preparation, 14% DS
Composition:

| | | |
|---|---|---|
| A | ® GENAPOL LRO liquid (Hoechst AG) | 35.00% |
| B | C12/14-DMAP-GA x lactic acid (Hoechst AG) | 7.60% |
| | ® GENAPOL PGL (Hoechst AG) | 4.00% |
| | Perfume oil | 0.30% |
| | Water | 53.10% |
| | Preservative | q.s. |
| | Dye solution | q.s. |
| C | Lactic acid | q.s. |

Preparation

| | |
|---|---|
| I | Stir into A the components of B one after the other. |
| II | Regulate the pH using C. |

Example 12

Clear shower gel, 14% DS
Composition:

| | | |
|---|---|---|
| A | ® GENAPOL LRO liquid (Hoechst AG) | 30.00% |
| B | C12/14-DMAP-GA x hydrochloric acid (Hoechst AG) | 8.40% |
| | ® GENAGEN CAB 818 (Hoechst AG) | 5.00% |
| | Perfume oil | 0.30% |
| | Water | 56.30% |
| | Preservative | q.s. |
| | Dye solution | q.s. |
| C | Hydrochloric acid | q.s. |

Preparation

| | |
|---|---|
| I | Stir into A the components of B one after the other. |
| II | Regulate the pH using C. |

Example 13

Clear antidandruff shampoo, 14% DS
Composition:

| | | |
|---|---|---|
| A | ®OCTOPIROX (Hoechst AG) | 0.50% |
| B | ®GENAPOL LRO liquid (Hoechst AG) | 35.00% |
| C | C12/14-DMAP-GA x hydrochloric acid (Hoechst AG) | 8.40% |
| | Perfume oil | 0.30% |
| | Water | 55.80% |
| | Preservative | q.s. |

-continued

| | | |
|---|---|---|
| D | Dye solution | q.s. |
| | Hydrochloric acid | q.s. |
| Preparation | | |
| I | Dissolve A in B. | |
| II | Stir into I the components of C one after the other. | |
| III | Regulate the pH using D. | |

Example 14
Clear hair shampoo, 14% DS
Composition:

| | | |
|---|---|---|
| A | ®GENAPOL LRO liquid (Hoechst AG) | 35.00% |
| B | C12/14-DMAP-GA x lactic acid (Hoechst AG) | 7.60% |
| | Perfume oil | 0.30% |
| | Water | 57.10% |
| | Preservative | q.s. |
| | Dye solution | q.s. |
| C | Lactic acid | q.s. |
| Preparation | | |
| I | Stir into A the components of B one after the other. | |
| II | Regulate the pH using C. | |

Example 15
Universal detergent

| Composition: | |
|---|---|
| Alkylsulfate | 12% |
| Soap | 1% |
| Fatty alcohol oxethylate | 4% |
| DMAP-GA | 3% |
| Sodium carbonate | 6% |
| Filosilicate SKS-6 | 14% |
| Zeolite | 14% |
| Sodium citrate | 5% |
| Sodium sulfate | 2% |
| Sodium percarbonate | 20% |
| Bleach activator | 4% |
| Polyacrylate (CP-5) | 6% |
| Enzymes | 1% |
| Water | ad 100% |

Example 16
Light-duty detergent

| Composition: | |
|---|---|
| Alkylbenzenesulfonate | 14% |
| Alkylsulfate | 8% |
| Soap | 2% |
| Fatty alcohol ethoxylate | 4% |
| DMAP-GA | 2% |
| Sodium carbonate | 1% |
| Filosilicate SKS-6 | 5% |
| Zeolite | 40% |
| Sodium sulfate | 14% |
| Enzymes | 1% |
| Water | ad 100% |

List of commercial products used:

| | |
|---|---|
| ®Genapol LRO liquid | $C_{12}/C_{18}$-alkyl diglycol ether sulfate, sodium salt (about 27% DS) |
| ®Hostapur SAS 60 | Secondary alkanesulfonate, sodium salt (about 60% DS) |
| ®Genapol SBE | $C_{12}/C_{18}$-alkylpolyglycol ether sulfosuccinate, disodium salt (about 40% DS) |
| ®Medialan LD | Fatty acid sarcoside, sodium salt (about 30% DS) |
| ®Genapol TSM | Alkyl ether sulfate and pearlizing agents |
| ®Genapol OA 080 | $C_{12}/C_{14}$-fatty alcohol ethoxylate containing 8 EO |
| ®Genagen CAB 818 | Alkylamidopropylbetaine (about 30% DS) |
| ®Hostapon KCG | N-cocoylglutamic acid, monosodium salt (about 25% DS) |
| PEG 400 | Polyethylene glycol (molar mass about 400) |
| ®Octopirox | 1-Hydroxy-4-methyl-6-(2,4,4-trimethylpentyl)-2(1H)pyridinone, 2-aminoethanol salt (antidandruff agent) |

Performance Investigations

The foaming behavior, the calcium tolerability and the wetting power of various surfactants including DMAP-GA were tested.

1. Foaming Ability

The foaming ability of the following surfactants:

DMAP-GA,

APG ($C_{12}/C_{14}$-alkyl polyglycoside),

CAPB ($C_8/C_{18}$-cocoalkylamidopropylbetaine)

was tested using the Ross-Miles method at 37° C. in water with varying calcium hardness. The concentration of the surfactants in the water was in each case 0.3 g/l. In an additional test, 1 ml of grease (Crisco+olive oil, 1:1) was added in each case. The following values were measured (foam height in mm):

| | | DMAP-GA | APG | CAPB |
|---|---|---|---|---|
| 1 | 0° Gh | 140 | 50 | 180 |
| 2 | 0° Gh | 90 | 50 | 70 |
| 3 | 3° Gh | 140 | 20 | 180 |
| 4 | 3° Gh | 90 | 20 | 80 |
| 5 | 15° Gh | 150 | 20 | 180 |
| 6 | 15° Gh | 110 | 15 | 80 |
| 7 | 25° Gh | 150 | 20 | 180 |
| 8 | 25° Gh | 80 | 15 | 80 |

(Gh = German hardness)

The results in lines 1, 3, 5 and 7 give the foam height without grease, and the results in lines 2, 4, 6 and 8 give the foam height with the addition of grease.

Using the same method, DMAP-GA-containing mixtures of the following composition were tested:
I. 1 part of DMAP-GA+4 parts of a mixture of 7 parts of $C_{12}/C_{14}$-lauryl ether sulfate+2 EO and 3 parts of $C_8/C_{18}$-cocoalkylamidopropylbetaine;
II. 1 part of $C_{12}/C_{14}$-alkyl polyglycoside+4 parts of a mixture of 7 parts of $C_{12}/C_{14}$-lauryl ether sulfate+2 EO and 3 parts of $C_8/C_{18}$-cocoalkylamidopropylbetaine.

| | | I | II |
|---|---|---|---|
| 1 | 0° Gh | 160 | 175 |
| 2 | 0° Gh | 75 | 40 |
| 3 | 3° Gh | 170 | 180 |
| 4 | 3° Gh | 170 | 145 |

-continued

|   |        | I   | II  |
|---|--------|-----|-----|
| 5 | 15° Gh | 160 | 190 |
| 6 | 15° Gh | 145 | 80  |
| 7 | 25° Gh | 150 | 190 |
| 8 | 25° Gh | 130 | 110 |

(Gh = German hardness)

The results in lines 1, 3, 5 and 7 give the foam height without grease, and the values in lines 2, 4, 6 and 8 give the foam height with the addition of grease.

In addition, the Ross-Miles foaming ability of the following acid addition products was measured:
a) $C_{12}/C_{14}$-DMAP-GA*lactic acid adduct
b) $C_{12}/C_{14}$-DMAP-GA*HCl adduct
c) $C_{16}/C_{18}$-DMAP-GA*lactic acid adduct
d) $C_{16}/C_{18}$-DMAP-GA*HCl adduct

|       | Foam height in mm | | | |
|-------|---------|---------|---------|---------|
|       | a)      | b)      | c)      | d)      |
| 1.0   | 250/250 | 245/245 | 185/180 | 190/190 |
| 0.1   | 195/195 | 200/195 | 160/160 | 150/145 |
| 0.03  | 35/10   | 45/15   | 65/65   | 80/75   |
| 0.006 | 15/5    | 10/5    | 15/10   | 25/25   |
| 0.002 | 5/0     | 5/0     | 15/10   | 15/10   |
| Foam volume in ml | | | | |
| 1.0   | 450/440 | 520/510 | 80/70   | 130/120 |

Test conditions: temperature 37° C., water hardness 15°Gh; pH=7

The first number in each case gives the initial measured value, and the second number in each case gives the measured value after 5 minutes.

The test results show that the acid adducts also have very good foaming behavior.

All the figures give the foam height in mm.

The Ross-Miles tests show that DMAP-GA, both as a free amidoamine and also as an acid adduct, have very good foaming ability alone and also as mixtures of these surfactants with cosurfactants, even in the presence of grease.

2. Calcium Tolerability

The resistance of the surfactants to hard water was determined by preparing solutions with increasing concentrations of the surfactant having 3 mmol/l, 4.5 mmol/l and 6 mmol/l of calcium hardness and, after not less than one hour and not more than two hours, observing whether opalescence or cloudiness have developed or even whether precipitates have formed. The results are evaluated using the mean of the summed individual values (5=clear; 4=opalescent; 3=cloudy; 2=slight precipitation; 1=heavy precipitation).

| DMAP-GA | $C_{12}/C_{14}$-glucamide | APG | CAPB | $C_{12}$-sarcosinate |
|---------|---------------------------|-----|------|----------------------|
| 5       | 2                         | 3   | 5    | 2                    |

The determination of the resistance to hard water shows that the surfactants and surfactant mixtures according to the invention have very good calcium tolerability.

3. Wetting Power (DIN ISO 8022)

The immersion wetting power is a measure of the ability of a surfactant solution to displace air present in a fabric when the fabric is dipped into the solution. The immersion wetting power of a surfactant is determined by determining the wetting time using a cotton swab in a surfactant solution of known concentration.

| Surfactant | Wetting time (seconds) |
|------------|------------------------|
| $C_{12}/C_{14}$-DMAP-GA *lactic acid | 290 |
| $C_{12}/C_{14}$-DMAP-GA *HCl | 250 |
| $C_{16}/C_{18}$-DMAP-GA *lactic acid | >300 |
| $C_{16}/C_{18}$-DMAP-GA *HCl | >300 |
| DMAP-GA | >300 |
| APG | 120 |
| GA | 100 |
| CAPB | 50 |
| $C_{12}$-sarcosinate | 40 |
| Na LES | 55 |

The determination of the wetting power shows that the surfactants of the formula 1 and their acid adducts and mixtures of these surfactants with other surfactants have a comparatively long wetting time. This finding is pleasing since good wetting behavior is usually also associated with a strong degreasing action.

The mildness to skin of the surfactants of the formula 1 and their acid adducts and mixtures of these surfactants with other surfactants is confirmed by determining the zein value and the red blood cell (RBC) value.

For DMAP-GA, a zein value of 39 mg of N/100 ml and an RBC value of 7% denaturation was measured. The values correspond to very good skin compatibility.

What is claimed is:

1. A surfactant-containing formulation comprising a compound of the formula (1)

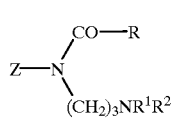

(1)

where R is an aliphatic radical having from 8 to 24 carbon atoms, $R^1$ and $R^2$, which are identical or different, are alkyl groups having from 1 to 4 carbon atoms or hydroxyalkyl groups having from 2 to 4 carbon atoms, and Z is a linear polyhydroxyhydrocarbon radical having at least 3 OH groups, which may also be alkoxylated, and also its acid addition products which additionally comprises one or more anionic, nonionic, cationic and/or amphoteric surfactants—before the period at the end of the sentence.

2. The surfactant-containing formulation as claimed in claim 1, wherein $R^1$ and $R^2$ are methyl, and Z is the residue of a sugar alcohol derived from a reducing mono- or disaccharide.

3. The surfactant-containing formulation as claimed in claim 2, wherein the reducing monosaccharide is glucose.

4. The surfactant-containing formulation as claimed in 1, which comprises compounds of the formula (1) in an amount of from 0.1 to 99% by weight.

5. The surfactant-containing formulation as claimed in claim 4, which comprises compounds of the formula (1) in an amount of from 1 to 50% by weight.

6. The surfactant-containing formulation as claimed in claim 1, in the form of a liquid light-duty detergent, universal detergent, manual dishwashing detergent, rinse aid, liquid cleaner and disinfectant, syndet soap, hair shampoo, hair rinse, hair colorant, hair-waving composition, foam bath, face cleanser, textile and fiber auxiliary, leather fat-liquoring agent, flotation auxiliary and auxiliary for sludge dewatering.

* * * * *